US010857101B1

(12) United States Patent
Millikin et al.

(10) Patent No.: US 10,857,101 B1
(45) Date of Patent: Dec. 8, 2020

(54) METHOD OF REDUCING CANNABIS PLANT MATTER

(71) Applicants: Rory Chesley Patrick Millikin, Kelowna (CA); Matthew Kennedy, Westminster, CA (US)

(72) Inventors: Rory Chesley Patrick Millikin, Kelowna (CA); Matthew Kennedy, Westminster, CA (US)

(73) Assignee: Drive Foods Corp, Westminster, CA (US)

( * ) Notice: Subject to any disclaimer, the term of this patent is extended or adjusted under 35 U.S.C. 154(b) by 0 days.

(21) Appl. No.: 16/752,609

(22) Filed: Jan. 24, 2020

Related U.S. Application Data

(63) Continuation-in-part of application No. 16/688,987, filed on Nov. 19, 2019.

(51) Int. Cl.
| | |
|---|---|
| *A61K 9/127* | (2006.01) |
| *A61K 8/14* | (2006.01) |
| *A61K 36/185* | (2006.01) |
| *A61K 8/9789* | (2017.01) |
| *A23P 10/35* | (2016.01) |
| *A23K 10/30* | (2016.01) |
| *A23K 40/30* | (2016.01) |
| *A23L 2/52* | (2006.01) |
| *A23L 19/00* | (2016.01) |

(52) U.S. Cl.
CPC ............ *A61K 9/1277* (2013.01); *A23K 10/30* (2016.05); *A23K 40/30* (2016.05); *A23L 2/52* (2013.01); *A23L 19/01* (2016.08); *A23P 10/35* (2016.08); *A61K 8/14* (2013.01); *A61K 8/9789* (2017.08); *A61K 36/185* (2013.01); *A23V 2002/00* (2013.01)

(58) Field of Classification Search
CPC .................................................... B02C 17/186
See application file for complete search history.

(56) References Cited

U.S. PATENT DOCUMENTS

| | | | |
|---|---|---|---|
| 10,213,788 B2 * | 2/2019 | Bates | A61K 36/185 |
| 2019/0241536 A1 * | 8/2019 | Durkacz | C07C 37/004 |
| 2019/0330532 A1 * | 10/2019 | Sunderland | D01F 9/16 |
| 2020/0078381 A1 * | 3/2020 | Delinski | A61K 31/685 |

FOREIGN PATENT DOCUMENTS

WO    WO-2019069309 A1 *   4/2019    ......... B01D 11/0203

OTHER PUBLICATIONS

Medical Marijuana Inc—Benefits of CBD Isolate Article, Published Jan. 12, 2019 (Year: 2019).*

(Continued)

*Primary Examiner* — Debra M Sullivan
*Assistant Examiner* — Matthew Kresse
(74) *Attorney, Agent, or Firm* — Christopher Pilling

(57) ABSTRACT

Improved methods for reducing whole plant *Cannabis* matter is provided. These various methods including reducing *Cannabis* plant matter to a nanoparticle powder. Reducing the particle size of *Cannabis* plant matter to a nano range difficult, and requires specific steps, as *Cannabis* plant matter is extremely sticky, and has a tendency to adhere and clump during the particle reduction size process. The whole *Cannabis* plant matter remains naturally green.

11 Claims, 4 Drawing Sheets

(56) References Cited

OTHER PUBLICATIONS

Marijuana Mommy—Marijuana Pill Making Video, Published Jun. 6, 2017 (Year: 2017).*
Grass City—Cannabis Reclaiming, Published Juky 15, 2012 (Year: 2012).*
Grass City—Cannabis Reclaiming, Published Jul. 15, 2012 (Year: 2012).*
Blood Brain Delivery Methods Using Nanotechnology, Author: Teleanu et al, Published Dec. 10, 2018 (Year: 2018).*

* cited by examiner

200

```
┌─────────────────────────────────────┐
│ Nanoparticulates are provided, where│in
│ the nanoparticulates are from whole │
│ plant cannabis plant matter         │
│ 201                                 │
└─────────────────────────────────────┘
                  │
                  ▼
┌─────────────────────────────────────┐
│ Adding a precoating to the          │
│ nanoparticulates                    │
│ 202                                 │
└─────────────────────────────────────┘
                  │
                  ▼
┌─────────────────────────────────────┐
│ Adding the precoated nanoparticulates│
│ to a liquid mixture                 │
│ 203                                 │
└─────────────────────────────────────┘
                  │
                  ▼
┌─────────────────────────────────────┐
│ Applying at least one energy force to│
│ the liquid mixture                  │
│ 204                                 │
└─────────────────────────────────────┘
                  │
                  ▼
┌─────────────────────────────────────┐
│ Suspending the nano-emulsified      │
│ encapsulated nanoparticulates into a│
│ liquid                              │
│ 205                                 │
└─────────────────────────────────────┘
```

*Fig. 2*

METHOD OF REDUCING CANNABIS PLANT MATTER

CROSS-REFERENCE TO RELATED APPLICATIONS

The present invention is a continuation in part application to U.S. Nonprovisional application Ser. No. 16/688,987, filed Nov. 19, 2019, herein disclosed in its entirety at least by reference.

BACKGROUND OF THE INVENTION

1. Field of the Invention

The present invention relates to plant matter, and more particular to a method of reducing *Cannabis* plant matter.

2. Description of Related Art

*Cannabis* as a health supplement has been practiced for over 1,000 years. Traditionally *Cannabis* is heated to release cannabinoids, primary tetrahydrocannabinol (THC) and cannabidiol (CBD). It is well known that cannabinoids offer many benefits to users, and there are a variety of methods to make cannabinoids available to the user.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In one aspect of the invention a method of processing *Cannabis* plant matter is provided, comprising steps: (a) drying the *Cannabis* plant matter to a moisture content below 15%; (b) reducing the dried *Cannabis* plant matter to create a powder.

In one embodiment, in step (b), the *Cannabis* plant matter is reduced using a mill. In another embodiment, in step (b), the *Cannabis* plant matter is reduced via grinding. In one embodiment, a step of sieving the reduced *Cannabis* plant matter, wherein the sieving is configured to capture matter over a first size. In one embodiment, the captured matter by the sieve is reduced again. In one embodiment, the reduced *Cannabis* plant matter contains particles smaller than 100 microns. In one embodiment, the reduced *Cannabis* plant matter has cannabinoid content greater than 1%. In one embodiment, a step of adding additional *Cannabis* plant matter to the powder to enhance its properties is provided. In one embodiment, a step of processing the powder into a pill form is provided. In another embodiment, a step of encapsulating the powder into a liposome for use in: tinctures, cosmetics, creams, animal feed, beverages, food, inhalation, medications, topicals, and hair loss applications is provided.

In another aspect of the invention, a method of processing *Cannabis* plant matter is provided comprising steps: (a) drying the *Cannabis* plant matter such that its moisture content remains above 5%; (b) processing the dried *Cannabis* plant matter to create a hardened form.

In one embodiment, a further step (c) adding a liquid to the hardened form to break the hardened form down into a mud or liquid is provided. In another embodiment, a step of drying the mud or liquid below 15% moisture content is provided. In another embodiment, a step of processing and reducing the dried mud or liquid into a powder. In one embodiment, the dried mud or liquid is reduced using a mill.

In yet another aspect of the invention, a method of processing *Cannabis* plant matter is provided, comprising steps: (a) adding the *Cannabis* plant matter to a liquid; (b) particle reducing the *Cannabis* plant matter while in the liquid; (c) drying the *Cannabis* plant matter liquid below 15% moisture content; (d) processing the *Cannabis* plant matter into powder.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which:

FIG. 2 is a flow diagram detailing method steps of a nano-emulsification encapsulation process according to an embodiment of the present invention; and, FIGS. 3A-B show a flow diagram detailing method steps of reducing *Cannabis* plant matter according to an embodiment of the present invention.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide a method of reducing *Cannabis* plant matter.

For the purpose of this disclosure, the word "a" is defined to mean "at least one." The word "*Cannabis*" is defined to mean "any species of the *Cannabis* genus of flowing plants including *Cannabis sativa, Cannabis indica, Cannabis ruderalis*, and hemp." The word "whole plant" or "whole *Cannabis* plant matter" is defined to mean "any portion of *Cannabis* plant matter provided without the use of an extraction method to obtain the portion of *Cannabis* plant matter." The word "powder" is defined to mean "particles containing *Cannabis* particles of 100 microns or less." The terminology includes the words above specifically mentioned, derivatives thereof, and words of similar import.

Reducing *Cannabis* plant matter to a small size, such as below 100 microns, or smaller, such as 120 nanometers, is very difficult and requires specific steps, as *Cannabis* plant matter is extremely sticky, and has a tendency to adhere and clump during the particle reduction size process. The *Cannabis* plant matter providing in the following method is whole plant, and has a cannabinoid content greater than 1%. Further, since the whole plant is used the *Cannabis* plant matter will have a naturally green color throughout the process, and likewise the end product will also be naturally green. It is well known that the green color comes from the pigment chlorophyll.

Figure 1:
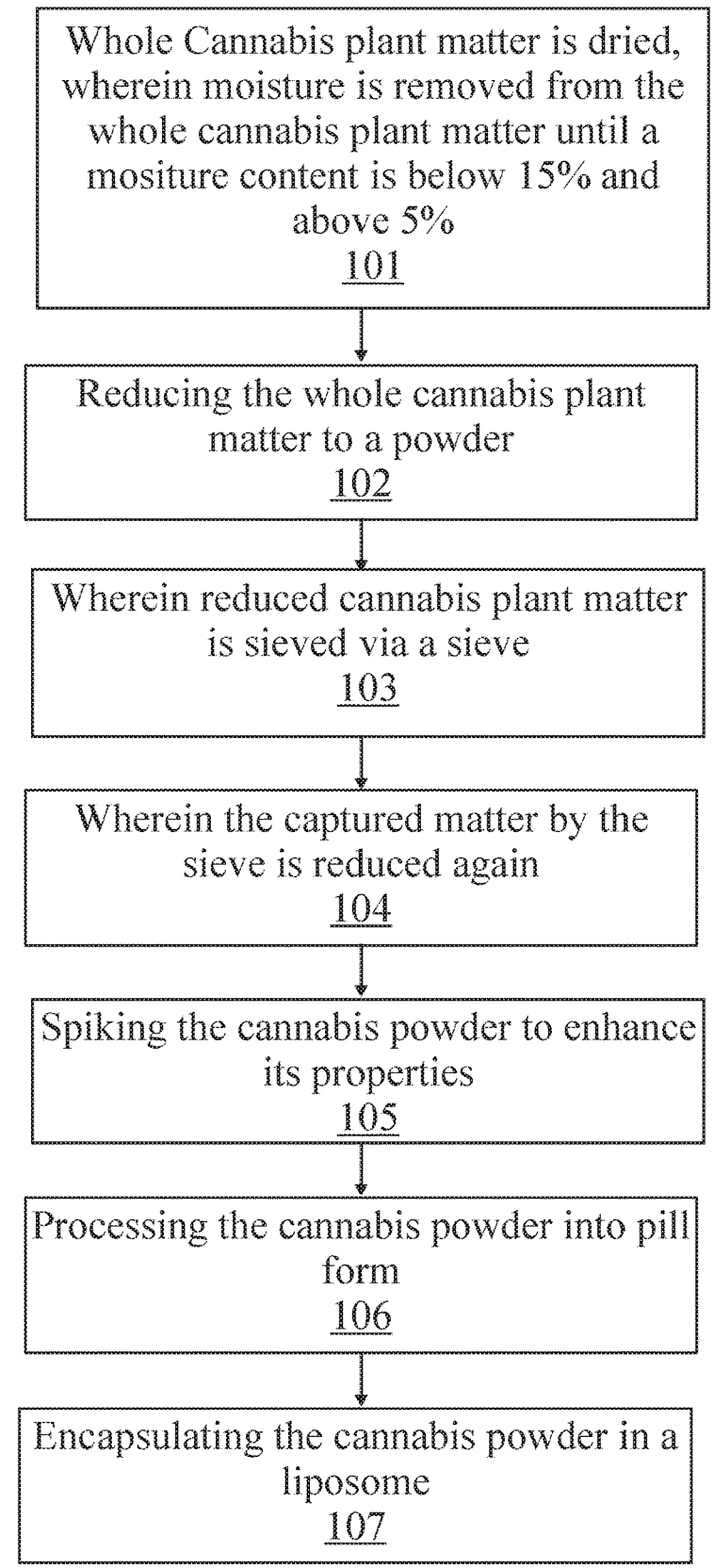
FIG. 1 is a flow diagram detailing method steps of reducing *Cannabis* plant matter according to an embodiment of the present invention.

Referring now to FIG. 1, a method 100 for reducing whole plant *Cannabis* plant matter is shown. In step 101, the whole *Cannabis* plant matter is dried, such that moisture is removed from the whole *Cannabis* plant matter until the *Cannabis* plant matter has a moisture content of at least below 15%. In some embodiments, the *Cannabis* plant matter should have a moisture content above 5%. The drying process may be any drying process known in the art. However, unexpectedly when using an aggressive drying technique, defined as applying physical pressure to the *Cannabis* plant matter, this prepares the *Cannabis* plant matter for the following steps by speeding up the drying process as well as reducing the stickiness of the plant matter, such that the *Cannabis* plant matter has a reduced tendency to clump in the following steps. In one embodiment, the aggressive drying technique is cold-pressing. The cold-pressing may be via hydraulic presses, rollers, or any other cold-pressing techniques known in the art. In alternative embodiments, other moisture removal techniques may be used, including but not limited to screw-pressing, masticating, triturating, centrifugal, or similar pressure techniques may be used. Alternatively, in other embodiments, vibration, sound waves, heat, or similar methods be used alone or in combination with any disclosed methods herein. In some embodiments, step 101 may be repeated to maximum the liquid content removed from the whole *Cannabis* plant matter and/or the moisture content is within the desired range, between 5-15% moisture content.

Next in step 102, the *Cannabis* plant matter is reduced to create a powder. In one embodiment, the *Cannabis* plant matter is reduced using a mill. In another embodiment, the *Cannabis* plant matter is reduced via grinding. In some embodiments, the *Cannabis* plant matter is reduced by way of blending, grinding, ball milling, knife milling, jet milling, or a combination thereof. Other methods known in the art to reduce the *Cannabis* plant matter may also be performed. For instance, in some embodiment, sound waves or vibrations are used to break up and reduce the particle size to create a powder. In one embodiment, the reduced powder contains particles smaller than 100 microns. In other embodiments, the reduced powder contains particles smaller than 120 nanometers. In alternative embodiments, in step 102 the *Cannabis* plant matter is processed to a powder. The *Cannabis* plant matter may be processed via a sieve to create a powder.

Next in step 103, the reduced *Cannabis* plant matter is sieved via a sieve to capture any matter that does not pass through the sieve. The yield defined as the amount of matter to pass through the sieve various depending on the technique used in step 102. For instance, milling techniques increase the yield more than other reduction methods, therefore milling is a preferred technique, however step 102 is not limited to milling.

Next in step 104, the captured matter by the sieve is reduced again via step 102. Then, the reduced matter may be sieved again via step 103. Next an optional step 105, includes "spiking" the *Cannabis* powder to enhance its properties. Spiking is defined as adding additional *Cannabis* plant matter. In some embodiments, the additional *Cannabis* plant matter is more *Cannabis* powder at a higher cannabinoid content than the original powder. In other embodiments, the additional *Cannabis* plant matter is a cannabinoid isolate. In other embodiments, the additional *Cannabis* plant matter is *Cannabis* plant matter that is used saturate the original powder. It is understood, that the additional *Cannabis* plant matter may be any *Cannabis* plant matter that is configured to enhance the *Cannabis* properties of the original powder or *Cannabis* plant matter. Enhancing the properties means improving and/or increasing the cannabinoid content, flavor, taste, constancy, size, etc.

Next in optional step 106, the *Cannabis* plant matter (powder) and any additional *Cannabis* plant matter is processed into a pill form. The pill is then available for use and consumption to an end user. Alternatively, in optional step 107, the *Cannabis* plant matter (powder) and any additional *Cannabis* plant matter is encapsulated in a fat, such as a liposome. Advantageously, the encapsulated liposome for use in tinctures, cosmetics, creams, animal feed, beverages, food, inhalation, medications, topicals, and hair loss applications.

In other applications, it is a particular object of the present invention to emulsify the plant matter particles (powder) into a liquid, including but not limited to water, oil, and any liquid containing water or oil, such as various beverages. However, the plant matter particles do not easily disperse in the liquid, as the nanoparticles tend to float. Reducing the *Cannabis* plant matter to as described, redistributes the plant cells of the plant matter. More specifically, grinding and milling the *Cannabis* plant matter into small size particulates allows the hydrophobic plants cells to be exposed in three dimensions. Therefore, the nanoparticulate has difficulty becoming wetted in water. Scientifically, the surface of the nanoparticulate is hydrophobic with low surface tension that does not allow water to spread smoothly around it. Therefore, it is a particular advantage of the present invention to utilize at least one surfactant or chemical to adjust and change the surface tension of the particulates, making it match that of the surrounding fluid better, such as water. This allows the particulates to distribute more uniformly and form a uniform slurry that does not contain sediments. In one embodiment, the at least on surfactant is lecithin, however other surfactants or chemicals may be used.

It is critical that the surface tension of the particulates matches the intended liquid. Since the plant particulates present a complicated surface, to get the best surface tension matching, it is desirable to have a special mixture of surface tension modulating molecules selected specifically for the *Cannabis* plant matter nanoparticulates. This is critical as *Cannabis* plant matter particles have unique characteristics compared to other plant matter. For instance, ground nano *Cannabis* is different from ground rose petals and different from seeds or roots used in spices.

The selection of molecules to modulate the surface tension of the *Cannabis* plant matter nanoparticulates is not obvious based on what is known about current emulsification technologies. Up to this point, the methods and processes disclosed herein are the first known methods to successfully perform the emulsification and encapsulation steps necessary to mix whole plant matter, i.e. not extracted plant matter, into a liquid that does not sediment.

During the emulsification and encapsulation process, in some embodiments, the dissolvable contents of whole plant *Cannabis* matter particles are extracted into the surrounding liquid and are also encapsulated by liposomes. In some embodiments, single layer encapsulation methods are used, using a mixture of phospholipids, sphingolipids, phosphatidylcholines, and phosphosphingolipids, or their derivatives and Tween™ (polysorbate) or Span™ (sorbitans) or their derivatives. In other embodiments, double layer encapsulation methods are used, also using a mixture of phospholipids, sphingolipids, phosphatidylcholines, and phosphosphingolipids, or their derivatives and Tween™ or Span™ or their derivatives. Preferred solvents used in encapsulation of extracted materials may be either oil and water-based. In other embodiments, alcohols such as ethanol, glycerin may be used, but not preferred. In some embodiments, high shear/high pressure homogenization and ultrasonication methods are used to effect the extraction of substances from plant matter. The emulsification and encapsulation process will be discussed in further details below.

Referring now to FIG. 2, one embodiment of a nano-emulsification encapsulation process 200 is shown. In step 201, the nanoparticulates (powder of a nano size, powder that contains particles less than 120 nanometers) from method 100 are provided (after step 105). Next in step 202, a precoating is added to the nanoparticulates. The precoating is selected from an oil or water-based substance depending on the indented use of the plant matter. The selection should be the inverse of the intended use. For instance, if the plant matter is intended to be mixed with a water-based liquid, the precoating should be an oil-based substance. Likewise, if the plant matter is intended to be mixed with an oil-based substance, the precoating should be a water-based substance. It should be understood, that step 202 is optional depending if a dry encapsulation or swollen encapsulation is desired.

Next in step 203, the precoated nanoparticulates are added to a liquid mixture. The mixture is configured to modulate the surface tension of the nanoparticulates. In one embodiment, mixture includes at least one predetermined chemical wherein the at least one chemical is selected from the list of lactylates, phospholipids, sphingolipids, phosphatidylcholines, phosphosphingolipids, and their derivatives. The at least one predetermined chemical is selected for use with a specific liquid in which the nanoparticles is intended to be mixed, for example, water, fruit juice, extracted and/or fermented drinks, alcoholic beverages, or similar. In other embodiments, the at least one predetermined chemical is selected for use the specific liquid in which the nanoparticles is intended to be mixed for use or in combination with a skin care product, for example, topical applications. In a preferred embodiment, when the specific liquid is water-based, the chemical is a phospholipid, such as soy lecithin.

Next in step 204, energy is provided to the liquid mixture via one or more of: heat, mechanical or sound, via one or more of sonication, high shear homogenization, and ultrasonication. At this point, the nano-emulsified and encapsulated plant matter may be stored for use. Finally, in some embodiments, in step 205, the nano-emulsified and encapsulated plant matter may be added and suspended in the intended application as previously mentioned, such as water, fruit juice, extracted and/or fermented drinks, alcoholic beverages, skin care products, or similar, then bottled and stored for use.

During the encapsulation process of encapsulating plant matter nanoparticulates into a liposome, it is critical that the treatment is mild to not disrupt the integrity of the plant cells making up the particulates. As previously mentioned, the molecules selected to create a liposome need to modulate the surface tension of the whole plant matter nanoparticle in order to match with the liquid. Since the particle surface is complex in texture and chemical nature, more than one type of molecules maybe needed. As previously mentioned, it is preferred, that soy lecithin is one of the chemicals used when the liquid is water-based. Others may be chosen from the list of lactylates, phospholipids, sphingolipids, phosphatidylcholines, and phosphosphingolipids, or their derivatives. If the liquid is an oil, it is preferred that Tween™ or Span™ or their derivatives be one of the chemicals, with the remainder chosen from the list of lactylates, phospholipids, sphingolipids, phosphatidylcholines, and phosphosphingolipids, or their derivatives. In other embodiments, synthetic lipids, synthetic surfactants, and their derivatives may be selected, such as pegylated polysorbate.

Figure 3A:
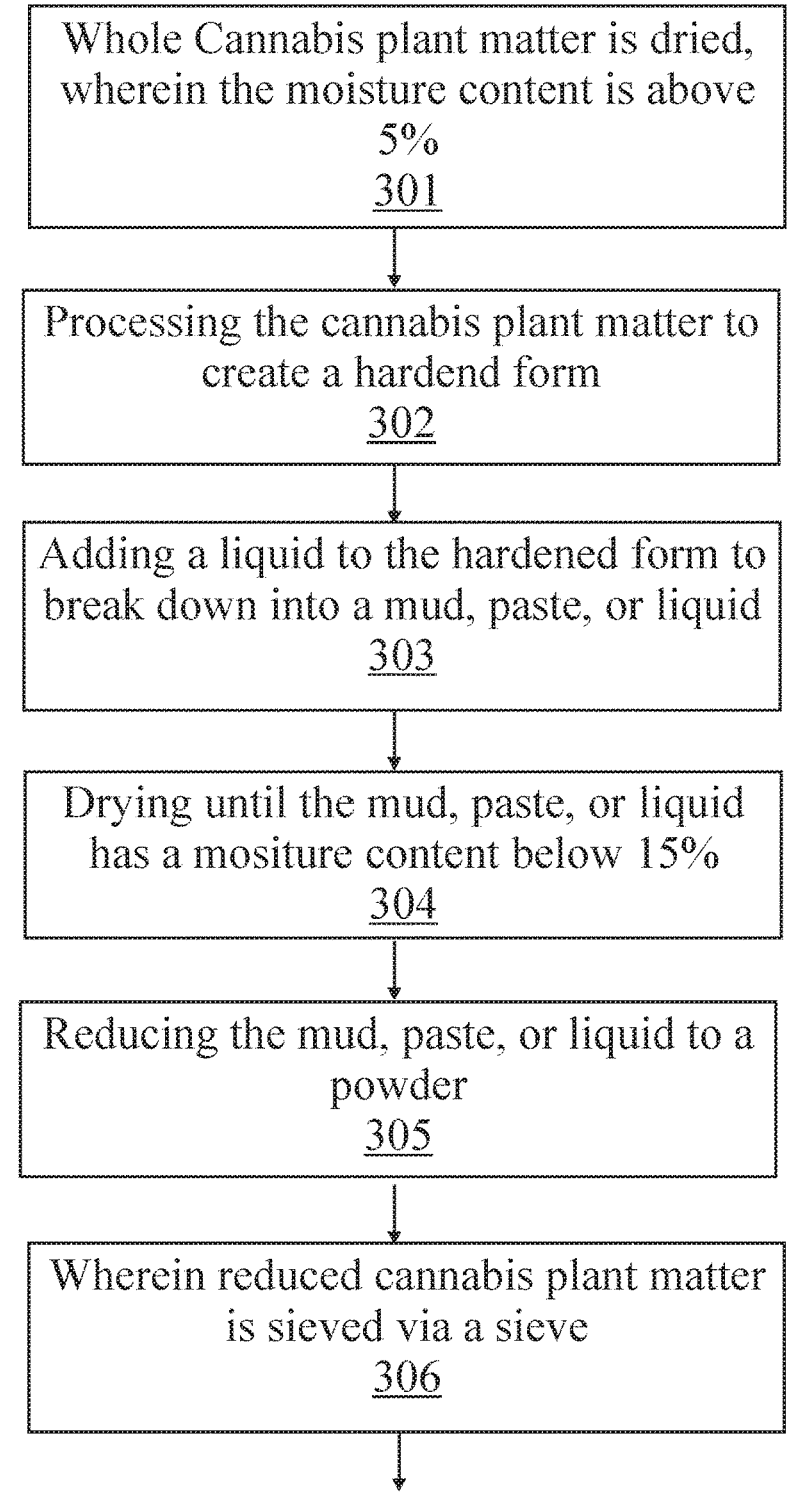
Figure 3B:
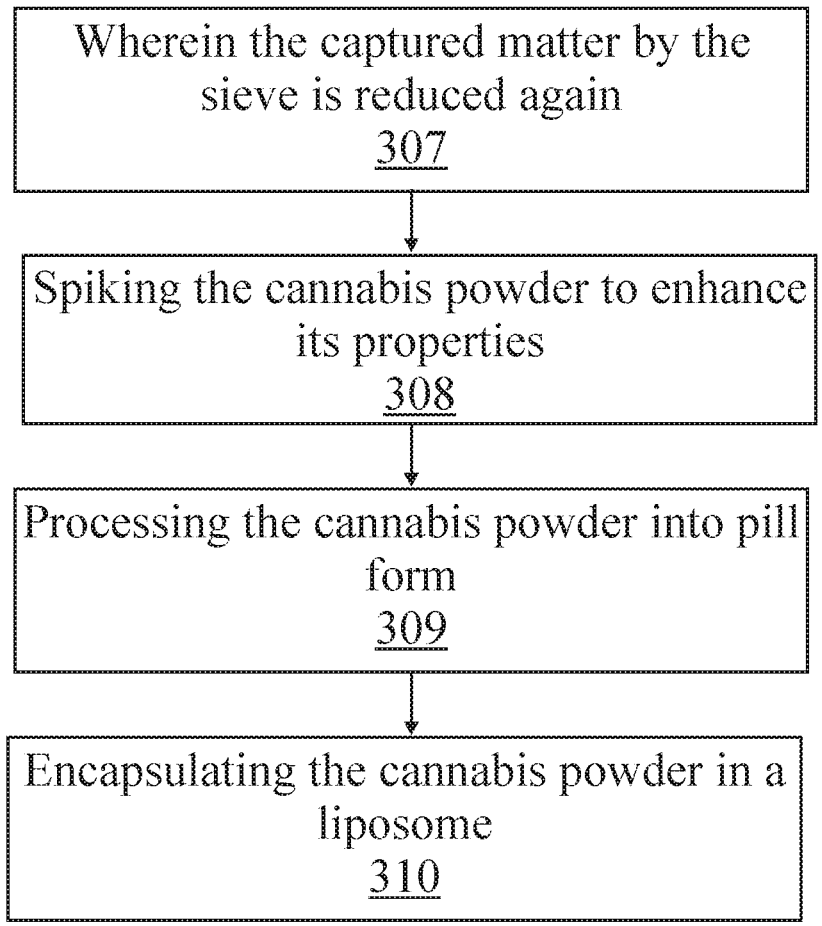

Referring now to FIGS. 3A-B, a method 300 for reducing whole plant *Cannabis* plant matter is shown. In step 301, the whole *Cannabis* plant matter is dried, however the *Cannabis* plant matter should have a moisture content above 5%. The drying methods may include any drying methods previously discussed.

Next in step 302, the dried whole *Cannabis* plant matter is processing to create a hardened form. The hardened form is defined as hardened powder that is clumped together. This is usually formed on the walls of the reducing machine, such as a mill. Next, in step 303, a liquid is added to the hardened form to break down into a mud, paste, or liquid. In some embodiments, the liquid is added directly to the reducing machine. Next, in step 304, the mud, paste, or liquid is dried such that the moisture content is below 15%. Next in step 305, the mud, paste, or liquid is reduced to create a powder. The reduction may be performed from any previously discussed method, machine, and technique. In one embodiment, the reduced powder contains particles smaller than 100 microns. In other embodiments, the reduced powder contains particles smaller than 120 nanometers.

Next in step 306, the reduced *Cannabis* plant matter is sieved via a sieve to capture any matter that does not pass through the sieve. The yield defined as the amount of matter to pass through the sieve various depending on the technique used in step 305. For instance, milling techniques increase the yield more than other reduction methods, therefore milling is a preferred technique; however step 305 is not limited to milling.

Next in step 307, the captured matter by the sieve is reduced again via step 102. Then, the reduced matter may be sieved again via step 206. Next an optional step 308, includes "spiking" the *Cannabis* powder to enhance its properties.

Next in optional step 309, the *Cannabis* plant matter (powder) and any additional *Cannabis* plant matter is processed into a pill form. The pill is then available for use and consumption to an end user. Alternatively, in optional step 310, the *Cannabis* plant matter (powder) and any additional *Cannabis* plant matter is encapsulated in a fat, such as a liposome. Advantageously, the encapsulated liposome for use in tinctures, cosmetics, creams, animal feed, beverages, food, inhalation, medications, topicals, and hair loss applications.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

What is claimed is:

1. A method of processing whole *Cannabis* plant matter comprising steps:
    (a) providing whole *Cannabis* plant matter, wherein the whole *Cannabis* plant matter is of a naturally green color;
    (b) drying the whole *Cannabis* plant matter to a moisture content below 15%;
    (c) reducing the dried whole *Cannabis* plant matter to create a powder without the use of an extraction method, wherein the powder is of a naturally green color and contains particles 120 nanometers or smaller.
2. The method of claim 1, wherein in step (c), the whole *Cannabis* plant matter is reduced using a mill.
3. The method of claim 1, further comprising a step of adding additional *Cannabis* plant matter to the powder to enhance its properties.
4. The method of claim 1, further comprising a step of processing the powder into a pill form.
5. The method of claim 1, further comprising a step of encapsulating the powder into a liposome for use in: tinctures, sprays, cosmetics, creams, animal feed, beverages, food, inhalation, medications, topicals, and hair loss applications.
6. A method of processing whole *Cannabis* plant plant matter comprising steps:
    (a) providing whole *Cannabis* plant matter, wherein the *Cannabis* plant matter is of a naturally green color and the whole *Cannabis* plant matter has a cannabinoid content greater than 1%;
    (b) adding the whole *Cannabis* plant matter to a liquid;
    (c) particle reducing the whole *Cannabis* plant matter while in the liquid;
    (d) drying the whole *Cannabis* plant matter liquid below 15% moisture content;
    (e) processing the whole *Cannabis* plant matter into powder without the use of an extraction method, wherein the powder contains particles 120 nanometers or smaller.
7. The method of claim 6, wherein in step (e), wherein the whole *Cannabis* plant matter is particle reduced using a mill and the whole *Cannabis* plant matter is ground up.
8. The method of claim 6, further comprising a step of sieving the powder with a sieve.
9. The method of claim 6, further comprising a step of adding additional *Cannabis* plant matter to the powder to enhance its properties.
10. The method of claim 6, further comprising a step of processing the powder into a pill form.
11. The method of claim 6, further comprising a step of encapsulating the powder into a liposome for use in: tinctures, spray, cosmetics, creams, animal feed, beverages, food, inhalation, medications, topicals, and hair loss applications.

* * * * *